(12) United States Patent
Yu et al.

(10) Patent No.: US 9,790,287 B2
(45) Date of Patent: Oct. 17, 2017

(54) AMPHIPHILIC POLYMER

(71) Applicant: Kookmin University Industry Academy Cooperation Foundation, Seoul (KR)

(72) Inventors: Yeon-Gyu Yu, Seoul (KR); Moon-Hee Sung, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/616,635

(22) Filed: Jun. 24, 2015

(65) Prior Publication Data

US 2016/0060361 A1 Mar. 3, 2016

(30) Foreign Application Priority Data

Aug. 4, 2014 (KR) .................. 10-2014-0099708

(51) Int. Cl.
*C07K 17/08* (2006.01)
*C08K 5/00* (2006.01)
*C08G 69/08* (2006.01)
*C08G 69/10* (2006.01)

(52) U.S. Cl.
CPC ............. *C07K 17/08* (2013.01); *C08G 69/08* (2013.01); *C08G 69/10* (2013.01); *C08K 5/0008* (2013.01)

(58) Field of Classification Search
CPC ....................................................... C07K 17/08
See application file for complete search history.

(56) References Cited

U.S. PATENT DOCUMENTS

2008/0132440 A1* 6/2008 Sung .................. A61K 8/67
424/78.3
2010/0036093 A1* 2/2010 Uyama ............ A61K 47/48315
530/345

OTHER PUBLICATIONS

Matsusaki, M.; Hiwatari, K.; Higashi, M.; Kaneko, T.; Akashi, M. Chem. Lett. 2004, 33, 398-399. The Chemical Society of Japan.*

* cited by examiner

*Primary Examiner* — Michael Pepitone
(74) *Attorney, Agent, or Firm* — The PL Law Group, PLLC

(57) ABSTRACT

The present invention relates to an amphiphilic polymer which includes a large amount of hydrophilic structures and hydrophobic structures, and thereby effectively stabilizing a membrane protein having a hydrophobic surface in an aqueous solution. A method of preparing an amphiphilic polymer represented by Formula 1 includes reacting a poly-gamma-glutamic acid with a reaction product of a fluorescent dye, biotin, an alkyl carboxylic acid having 1 to 10 carbon atoms or a cycloalkyl carboxylic acid having 5 to 20 carbon atoms having a carboxyl group, and dicyclohexylcarbodiimide (DCC) and reacting the poly-gamma-glutamic acid with DCC after reacting the poly-gamma-glutamic acid with the reaction product, and reacting the poly-gamma-glutamic acid with a hydrophilic amine and a hydrophobic amine.

8 Claims, 7 Drawing Sheets

AMPHIPHILIC POLYMER

CROSS-REFERENCE TO RELATED APPLICATION

This application claims priority to and the benefit of Korean Patent Application No. 10-2014-0099708, filed on Aug. 4, 2014, the disclosure of which is incorporated herein by reference in its entirety.

BACKGROUND

1. Field of the Invention

The present invention relates to an amphiphilic polymer.

2. Discussion of Related Art

In proteins of a human body, a membrane protein which is present in a cell membrane accounts for 30% or more of the total genome. Particularly, a receptor such as a G-protein coupled receptor (GPCR) or an ion channel protein is responsible for a signal pathway in the living body, is involved in various diseases such as cancer, nervous system disorders, immune diseases, inflammatory diseases or the like, accounts for 60% or more of drug targeting, and occupies an important position in disease diagnosis and new drug development. The function of the above-described membrane protein is induced by an interaction with other molecules such as a ligand. Accordingly, in order to analyze the interaction between the membrane protein and the ligand or the like, a technique of preparing the refined membrane protein having an active structure and a technique of fixing the membrane protein to a support are core technologies to analyze binding specificity between the membrane protein and ligand, and are essential for the applications in biotechnology.

Although a large number of techniques have been developed for the stabilization and fixation of proteins, techniques for the refinement as well as the stabilization and fixation of the membrane protein are highly limited due to structural characteristics of the membrane protein. In the case of a water soluble protein, hydrophilic amino acid residues are mainly exposed to a surface of proteins, interact with water molecules, and thus may be easily stabilized. On the other hand, the membrane protein has many hydrophobic surfaces formed of hydrophobic residues, and thus forms a stable structure when the membrane protein is present at a lipid bilayer, positioned adjacent to hydrophobic sites of the lipid. However, when the membrane protein is present in an aqueous solution without the lipid, the hydrophobic surfaces of the membrane protein aggregate to each other without interacting with the water molecules, and thereby forming insoluble precipitates which are inactive. Accordingly, detergents which are water-soluble and are capable of stabilizing the hydrophobic surfaces of the membrane protein are required in the refinement process for research on the function of the membrane protein.

Suitable detergents are bound to the hydrophobic surfaces of the membrane protein while the active structure of the membrane protein is maintained, and thereby allow the membrane protein to maintain the active structure in the aqueous solution without aggregating to each other. However, in many types of the commercially available detergents, the number of the detergents allowing the specific membrane protein to be active in the aqueous solution is small, and a process of determining the above-described detergents is complicated. For example, few types of detergents are capable of allowing receptor proteins such as a GPCR to maintain the active structure in the aqueous solution, and although b-octylglucoside (OG) and dodecyl-maltoside (DDM) are known to have a great effect in stabilizing the membrane protein under circumstances of the aqueous solution (Journal of Biological Chemistry, 2001, vol 276, pp 32403-32406. Protein Expression and Purification 2012, vol. 86 pp 12-20), the above-described detergents may not be widely applied to all membrane proteins, and a high cost is required therefor.

In addition to the detergents, methods of forming a bicelle (Analytical Biochemistry, 2000, vol. pp284, 327-333) and a nanodisc (Nano Letter 2002, vol 2, pp 853-856) using lipids and detergents or lipids and lipid-stabilizing proteins, respectively, are used as a method of stabilizing the membrane protein in the aqueous solution. According to these methods, the membrane protein forms a structure having a size of several nanometers in a similar environment to the lipid bilayer, the membrane proteins may be maintained in a state of the aqueous solution under the lipid layer environment. However, a manufacturing process of the above-described method is complicated, and a high coat is required therefor.

A method of stabilizing the membrane protein using a polymer has also been known. The polymer referred to as an amphipol is a polymer which has both hydrophobic sites and hydrophilic sites in one polymer molecule by introducing an alkyl group into a polyacrylic acid, and has been reported to have a high effect in the membrane protein stabilization (Biochemistry, 2006, vol. 45, pp 13954-13961). However, the above-described polymer has a low production yield, and lipid layer-reassembling activity of the membrane protein has not yet been reported. Further, the manufacturing cost is high due to a low synthesis yield of the amphipol, and the lipid layer-reassembling function of the membrane protein with the amphipol has not yet been reported. Further, when the amphipol is used, a process of introducing a functional group such as a fluorescent material, biotin, or the like which may be used in the process of property analysis and fixation of the proteins to a specific site of the polymer is complicated and difficult.

Accordingly, there is a need for techniques of stabilizing the membrane protein in the aqueous solution which may be widely applied to the membrane proteins such as receptor proteins and ion channel proteins which serve an important role in the living body and are target proteins in new drug development. The embodiment of the present invention is intended to develop a method of preparing a polymer which is an amphiphilic polymer having both hydrophilic and hydrophobic sites, and includes a functional group for fixation at the same time by introducing the functional group for fixation, a hydrophobic functional group, and a hydrophilic functional group into a poly-glutamic acid, and is intended to develop techniques of the membrane protein stabilization, the membrane protein fixation, and lipid layer-reassembling of the membrane protein.

SUMMARY

An embodiment of the present invention is directed to providing an amphiphilic polymer which may be used to stabilize a membrane protein in an aqueous solution.

An embodiment of the present invention is directed to providing a method of preparing the amphiphilic polymer.

An embodiment of the present invention is directed to providing a method of stabilizing a membrane protein using the amphiphilic polymer.

An embodiment of the present invention is directed to providing a membrane protein-fixed substrate using the amphiphilic polymer.

An embodiment of the present invention is directed to providing a reconstitution method of a membrane protein into lipid bilayer environment.

According to an aspect of the present invention, there is provided an amphiphilic polymer, represented by the following Formula 1:

[Formula 1]

$$HNR_1-\underset{H}{\overset{COR_2}{C}}-\overset{H_2}{C}-\overset{H_2}{C}-\underset{\parallel}{\overset{}{C}}-\left[\underset{H}{N}-\underset{H}{\overset{COR_3}{C}}-\overset{H_2}{C}-\overset{H_2}{C}-\underset{\parallel}{\overset{}{C}}\right]_n-\underset{H}{N}-\underset{H}{\overset{COR_4}{C}}-\overset{H_2}{C}-\overset{H_2}{C}-COR_5$$

(where, $R_1$ may be a fluorescent dye, a biotin group, an alkyl group having 1 to 10 carbon atoms, or a cycloalkyl carbonyl group having 5 to 20 carbon atoms; $R_2$, $R_3$, $R_4$ and $R_5$ may have a structure independently derived from a hydroxy group, or a hydrophilic or hydrophobic amine, repeated units of $R_3$ may have identical or different structures, one or more of repeated units of $R_3$ may have a structure derived from a hydrophilic amine, one or more of repeated units of $R_3$ may have a structure derived from a hydrophobic amine; and n may be an integer in a range of 1 to 1,000)

The fluorescent dye may be one or more types selected from the group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), and Texas Red.

The hydrophilic amine may be an alkyl amine having 1 to 10 carbon atoms or a cycloalkyl amine having 5 to 20 carbon atoms, which is substituted with a hydroxy group or an amino group.

The hydrophobic amine may be an alkyl amine having 1 to 10 carbon atoms or a cycloalkyl amine having 5 to 20 carbon atoms.

A mole ratio of a structure derived from the hydrophilic amine to a structure derived from the hydrophobic amine may be in a range of 1:9 to 9:1.

The amphiphilic polymer according to an embodiment of the present invention may have a weight-average molecular weight in a range of 5,000 to 50,000.

According to another aspect of the present invention, there is provided a method of preparing an amphiphilic polymer represented by the following Formula 1, including: reacting a poly-gamma-glutamic acid with a reaction product of a fluorescent dye, biotin, an alkyl carboxylic acid having 1 to 10 carbon atoms or a cycloalkyl carboxylic acid having 5 to 20 carbon atoms having a carboxyl group and dicyclo-hexylcarbodiimide (DCC); and reacting the poly-gamma-glutamic acid with DCC after reacting the poly-gamma-glutamic acid with the reaction product, and reacting the poly-gamma-glutamic acid with the hydrophilic amine and hydrophobic amine.

[Formula 1]

$$HNR_1-\underset{H}{\overset{COR_2}{C}}-\overset{H_2}{C}-\overset{H_2}{C}-\underset{\parallel}{\overset{}{C}}-\left[\underset{H}{N}-\underset{H}{\overset{COR_3}{C}}-\overset{H_2}{C}-\overset{H_2}{C}-\underset{\parallel}{\overset{}{C}}\right]_n-\underset{H}{N}-\underset{H}{\overset{COR_4}{C}}-\overset{H_2}{C}-\overset{H_2}{C}-COR_5$$

(where, $R_1$ may be a fluorescent dye, a biotin group, or an alkyl group having 1 to 10 carbon atoms, or a cycloalkyl carbonyl group having 5 to 20 carbon atoms; $R_2$, $R_3$, $R_4$ and $R_5$ may have a structure independently derived from a hydroxy group, or a hydrophilic or hydrophobic amine, repeated units of $R_3$ may have identical or different structures, one or more of repeated units of $R_3$ may have a structure derived from a hydrophilic amine, and one m or more of repeated units of $R_3$ may have a structure derived from a hydrophobic amine; and n may be an integer in a range of 1 to 1,000)

The fluorescent dye may be one or more types selected from the group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), and Texas Red. The hydrophilic amine may be an alkyl amine having 1 to 10 carbon atoms or a cycloalkyl amine having 5 to 20 carbon atoms, which is substituted with a hydroxy group or an amino group.

The hydrophobic amine may be an alkyl amine having 1 to 10 carbon atoms or a cycloalkyl amine having 5 to 20 carbon atoms.

According to another aspect of the present invention, there is provided a method of stabilizing a membrane protein, which includes forming a membrane protein-amphiphilic polymer complex by binding a membrane protein in an aqueous solution to the above-described amphiphilic polymer.

A hydrophobic interaction between a structure derived from a hydrophobic amine of the amphiphilic polymer and a hydrophobic surface of a membrane protein may be performed, and a structure derived from a hydrophilic amine may increase solubility of the membrane protein in an aqueous solution.

According to another aspect of the present invention, there is provided a membrane protein-fixed substrate, including avidin or streptavidin attached on a base material, and a complex of a membrane protein and an amphiphilic polymer represented by the following Formula 2 which is bound to the avidin or streptavidin:

[Formula 2]

$$HNR_1-\underset{H}{\overset{COR_2}{C}}-\overset{H_2}{C}-\overset{H_2}{C}-\underset{\parallel}{\overset{}{C}}-\left[\underset{H}{N}-\underset{H}{\overset{COR_3}{C}}-\overset{H_2}{C}-\overset{H_2}{C}-\underset{\parallel}{\overset{}{C}}\right]_n-\underset{H}{N}-\underset{H}{\overset{COR_4}{C}}-\overset{H_2}{C}-\overset{H_2}{C}-COR_5$$

(where, $R_1$ may be a biotin group; $R_2$, $R_3$, $R_4$ and $R_5$ may have a structure independently derived from a hydroxy group, or a hydrophilic or hydrophobic amine, repeated units of $R_3$ may have identical or different structures, one or more of repeated units of $R_3$ may have a structure derived from a hydrophilic amine, and one or more of repeated units of $R_3$ may have a structure derived from a hydrophobic amine; and n may be an integer in a range of 1 to 1,000)

According to another aspect of the present invention, there is provided a method of restoring a structure of a membrane protein, which includes adding the above-described amphiphilic polymer to a modified membrane protein.

The modified membrane protein is induced by adding a detergent to a membrane protein.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present invention relates to an amphiphilic polymer which includes a large amount of hydrophilic structures and hydrophobic structures, and thereby effectively stabilizes a membrane protein having a hydrophobic surface in an aqueous solution.

Hereinafter, the present invention will be described in detail.

The present invention provides a novel amphiphilic polymer.

The amphiphilic polymer according to an embodiment of the present invention is represented by the following Formula 1.

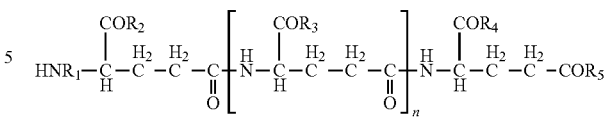

[Formula 1]

(where, $R_1$ is a fluorescent dye, a biotin group, an alkyl group having 1 to 10 carbon atoms, or a cycloalkyl carbonyl group having 5 to 20 carbon atoms; $R_2$, $R_3$, $R_4$ and $R_5$ have a structure independently derived from a hydroxy group, or a hydrophilic or hydrophobic amine, repeated units of $R_3$ have identical or different structures, one or more of repeated units of $R_3$ have a structure derived from a hydrophilic amine, one or more of repeated units of $R_3$ have a structure derived from a hydrophobic amine; and n is an integer in a range of 1 to 1,000)

Figure 1:
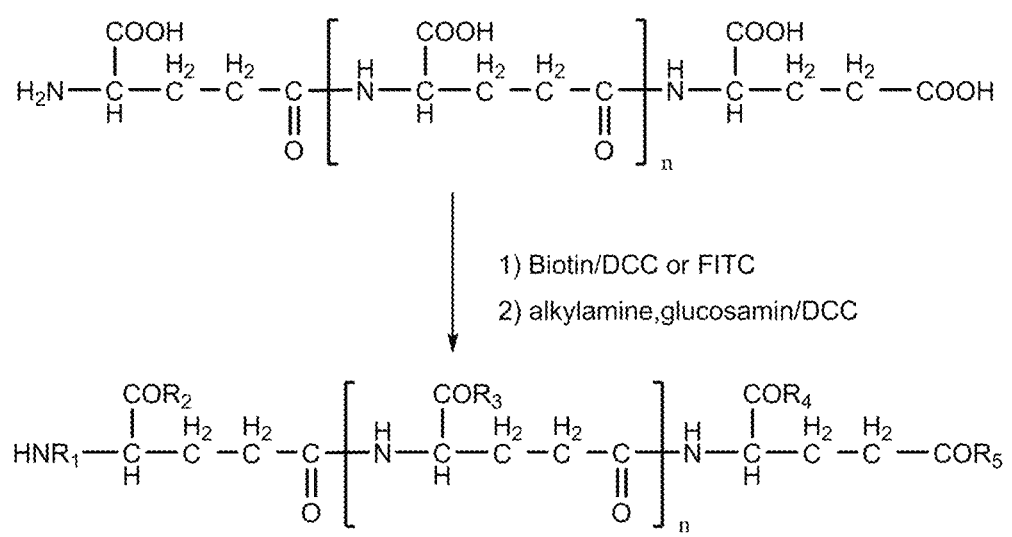
FIG. 1 is a schematic view of synthesis of an amphiphilic polymer according to an embodiment of the present invention from a poly-gamma-glutamic acid.

The amphiphilic polymer according to the embodiment of the present invention has a structure in which a poly-gamma-glutamic acid is provided as a frame, an amide bond is formed by polymerization between an N-terminal amino group of the poly-gamma-glutamic acid and a fluorescent dye, biotin, an alkyl carboxylic acid having 1 to 10 carbon atoms, or a cycloalkyl carboxylic acid having 5 to 20 carbon atoms, and an amide bond is formed by polymerization between a carboxyl group of the C-terminal of a repeated unit of the glutamic acid, and a hydrophilic or hydrophobic amine (FIG. 1).

The amphiphilic polymer according to the embodiment of the present invention has both a hydrophilic structure derived from the hydrophilic amine and a hydrophobic structure derived from the hydrophobic amine. Accordingly, the amphiphilic polymer may also be used to stabilize a membrane protein to maintain an original active structure in an aqueous solution.

Specifically, the membrane protein is a protein which is in a cell membrane, and is involved in cell growth and differentiation, thereby being involved in various diseases. The membrane protein is difficult to be extracted from a cell membrane, has a hydrophobic surface in contrast with water soluble proteins present in cells, and thus the hydrophobic surfaces aggregate to each other in a state of the aqueous solution after extraction, forming insoluble precipitates which have no activity. Accordingly, the structure and function analyses of the membrane protein are difficult.

Figure 2:
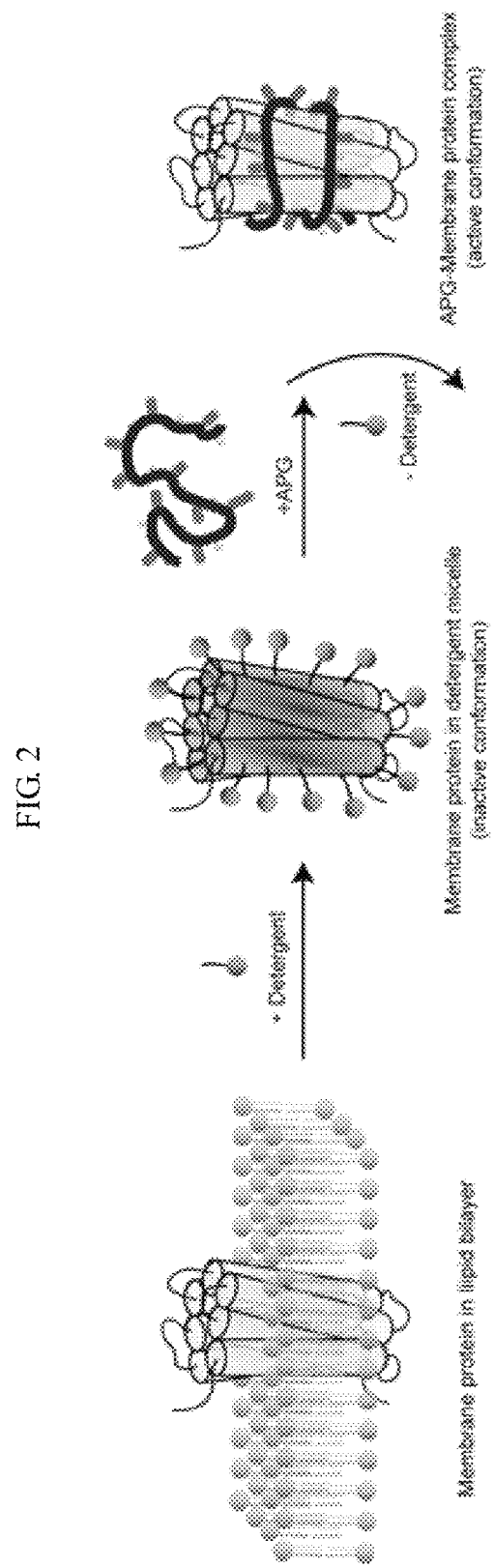
FIG. 2 is a view schematically illustrating a process of stabilizing a membrane protein by the amphiphilic polymer.

However, since the polymer according to the embodiment of the present invention has both of a hydrophilic structure and a hydrophobic structure, when the polymer is added to the membrane protein in the aqueous solution, a membrane protein-amphiphilic polymer complex is formed because the polymer surrounds a membrane protein surface by a hydrophobic interaction between hydrophobic structures of the polymer and the membrane protein surface. Further, the hydrophilic structure of the polymer improves solubility of the complex in the aqueous solution, and thus aggregation of hydrophobic sites in the aqueous solution may be prevented (FIG. 2).

The poly-gamma-glutamic acid is a highly hydrophilic and bio-compatible polymer in which an amine of an alpha-carbon of the glutamic acid and a carboxyl group of a gamma-carbon are connected by a peptide-bond. For example, the poly-gamma-glutamic acid having a weight-average molecular weight of 10,000 has about 78 carboxyl groups and a plurality of sites capable of binding to a hydrophilic or hydrophobic structure, each carboxyl group is spaced apart by a gamma-glutamic acid unit, and thus a large amount of hydrophilic and hydrophobic structures may be introduced while minimizing an influence of steric resistance.

The hydrophilic amine is not particularly limited as long as the hydrophilic amine has a hydrophilic group such as a hydroxy group, an amino group, or the like, and shows hydrophilicity, and for example, the hydrophilic amine may be an alkyl amine having 1 to 10 carbon atoms or a cycloalkyl amine having 5 to 20 carbon atoms which is substituted with a hydroxy group or an amino group. One or a mixture of two or more types thereof may be used.

The hydrophobic amine may be an alkyl amine having 1 to 10 carbon atoms or a cycloalkyl amine having 5 to 20 carbon atoms, but is not limited thereto.

In the polymer according to the embodiment of the present invention, a mole ratio between a structure derived from the hydrophilic amine and a structure derived from the hydrophobic amine is not particularly limited, and for example, may be in the range of 1:9 to 9:1. When the mole ratio is in the above-described range, the polymer may show suitable hydrophilicity and hydrophobicity, and thus may sufficiently stabilize the membrane protein in the aqueous solution.

Further, the poly-gamma-glutamic acid has an N-terminal amino group, and when the polymer according to the embodiment of the present invention has a structure in which a fluorescent dye is bound to the N-terminal amino group, the membrane protein may be fluorescent-labeled, and thus analysis of the membrane protein may be further easily performed.

The fluorescent dye is not particularly limited as long as the fluorescent dye has a carboxyl group, and for example, one or more types selected from the group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), and Texas Red may be used, but is not limited thereto.

Further, when the polymer has a structure in which a biotin group is bound to the N-terminal amino group, biotin has an excellent binding force with respect to avidin and streptavidin, and thus the polymer may be used to fix the membrane protein to a base material on which avidin or streptavidin is attached.

A molecular weight of the amphiphilic polymer according to the embodiment of the present invention is not particularly limited, and may be suitably selected according to the molecular weight of the membrane protein to be stabilized. For example, a weight-average molecular weight of the polymer may be in the range of 5,000 to 50,000.

Further, the present invention provides a method of preparing the amphiphilic polymer.

In accordance with the method of preparing the amphiphilic polymer according to the embodiment of the present invention, first, a poly-gamma-glutamic acid is reacted with a reaction product of a fluorescent dye, biotin, an alkyl carboxylic acid having 1 to 10 carbon atoms, or a cycloalkyl carboxylic acid having 5 to 20 carbon atoms and dicyclohexylcarbodiimide (DCC).

The fluorescent dye may be the above-described fluorescent dye.

When the fluorescent dye, biotin, an alkyl carboxylic acid having 1 to 10 carbon atoms, or a cycloalkyl carboxylic acid having 5 to 20 carbon atoms having a carboxyl group is reacted with DCC, a compound in which the fluorescent dye, biotin, an alkyl carboxylic acid having 1 to 10 carbon atoms, or a cycloalkyl carboxylic acid having 5 to 20 carbon atoms having a carboxyl group are bound to DCC is obtained by a reaction of the carboxyl group and DCC.

Further, the reaction product is reacted with the poly-gamma-glutamic acid, condensation polymerization of the fluorescent dye, biotin, an alkyl carboxylic acid having 1 to 10 carbon atoms, or a cycloalkyl carboxylic acid having 5 to 20 carbon atoms having a carboxyl group and the N-terminal amino group of the poly-gamma-glutamic acid is performed, and thereby a structure formed of an amide bond is obtained.

The above-described reaction is performed with a high yield at room temperature, and occurs in a site-specific manner with respect to the N-terminal amino group.

Thereafter, the poly-gamma-glutamic acid reacted as above is reacted with DCC, and then is reacted with a hydrophilic amine and a hydrophobic amine.

When the poly-gamma-glutamic acid reacted as above is reacted with DCC, a structure in which DCC is bound to the carboxyl group of the repeated unit of the gamma-glutamic acid is obtained, and when the poly-gamma-glutamic acid is further reacted with the hydrophilic amine and hydrophobic amine, condensation polymerization of the hydrophilic and hydrophobic amine and the carboxyl group of the repeated unit of the gamma-glutamic acid is performed as described above, the amphiphilic polymer according to the embodiment of the present invention which is bound by an amide bond and represented by the following Formula 1 is obtained.

[Formula 1]

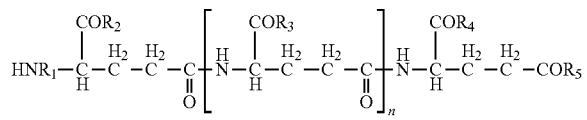

(where, $R_1$ is a fluorescent dye, a biotin group, an alkyl group having 1 to 10 carbon atoms, or a cycloalkyl carbonyl group having 5 to 20 carbon atoms; $R_2$, $R_3$, $R_4$ and $R_5$ have a structure independently derived from a hydroxy group, or a hydrophilic or hydrophobic amine, repeated units of $R_3$ have identical or different structures, one or more of repeated units of $R_3$ have a structure derived from a hydrophilic amine, one or more of repeated units of $R_3$ have a structure derived from a hydrophobic amine; and n is an integer in a range of 1 to 1,000)

Similarly, the reaction is performed with a high yield at room temperature, each carboxyl group is spaced apart by the repeated unit of the gamma-glutamic acid, and thus the decrease in the reactivity due to steric hindrance may be minimized.

The hydrophilic amine and hydrophobic amine may be the above-described hydrophilic amine and hydrophobic amine.

Further, the present invention provides a method of stabilizing a membrane protein using the amphiphilic polymer.

In the method of stabilizing the membrane protein according to the embodiment of the present invention, a membrane protein-amphiphilic polymer complex is formed by binding the membrane protein in an aqueous solution to the amphiphilic polymer.

As described above, since the amphiphilic polymer according to the embodiment of the present invention has both of the hydrophilic structure and the hydrophobic structure, a hydrophobic interaction between the hydrophobic structure derived from the hydrophobic amine of the amphiphilic polymer and the hydrophobic surface of the membrane protein is performed, the hydrophilic structure derived from the hydrophilic amine increases solubility of the membrane protein in the aqueous solution, and thereby preventing the membrane proteins from aggregating to each other and maintaining an activated structure in the aqueous solution.

Further, the present invention provides a membrane protein-fixed substrate.

The membrane protein-fixed substrate according to the embodiment of the present invention includes avidin or streptavidin attached to a base material, and a membrane protein-amphiphilic polymer complex which is bound thereto.

The amphiphilic polymer is represented by the following Formula 2.

[Formula 2]

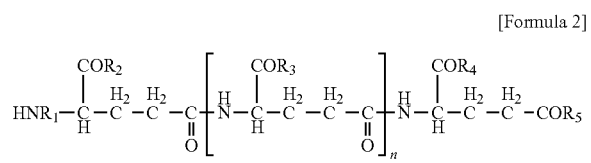

(where, $R_1$ is a biotin group; $R_2$, $R_3$, $R_4$ and $R_5$ have a structure independently derived from a hydroxy group, or a hydrophilic or hydrophobic amine, repeated units of $R_3$ have identical or different structures, one or more of repeated units of $R_3$ have a structure derived from a hydrophilic amine, and one or more of repeated units of $R_3$ have a structure derived from a hydrophobic amine; and n is an integer in a range of 1 to 1,000).

Biotin has a high chemical affinity with avidin and streptavidin, and has a strong binding force therebetween.

When the membrane protein-amphiphilic polymer complex contacts the base material to which avidin or streptavidin is attached, the membrane protein may be fixed to the substrate through the bond between a biotin group of the amphiphilic polymer and avidin or streptavidin attached to the base material.

A type and mole ratio of the hydrophilic and hydrophobic amine may be in the above-described range.

Further, the present invention provides a method of restoring a structure of membrane protein.

When the amphiphilic polymer is added to a modified membrane protein, an original active structure of the modified membrane protein may be restored.

A cause of the modification is not limited, and for example, the modification may be induced by adding a detergent. Hereinafter, the case in which the membrane protein is modified by adding the detergent will be described in detail as an example, but the cause of the modification is not limited thereto.

When a strong detergent such as SDS or the like is added to the membrane protein, the membrane protein is modified, and loses an original activity. When the amphiphilic polymer is added thereto, the membrane protein binds to the amphiphilic polymer, hydrophobic sites of the amphiphilic polymer stabilizes a hydrophobic surface of the membrane protein, the formation of the membrane protein structure is facilitated, and thereby an original active structure of the membrane protein is restored.

Further, the present invention provides a reconstitution method of a membrane protein into lipid bilayer environment.

Conventional detergent-dependent reconstitution process of membrane proteins in aqueous solution into lipid-bilayer environment such as liposomes and cell surface membrane accompanies disruption of lipid-bilayer structure. During this process the original shape of liposomes is destroyed, and the viability cell is significantly reduced. Membrane proteins stabilized by the amphiphilic polymer can be inserted into lipid-bilayer structure such as liposomes without solubilization of lipid-bilayer structure. Hence, the shape of liposomes during the amphiphilic polyer-dependent reconstitution is preserved which is beneficial for the functional assay of membrane protein.

Figure 8:
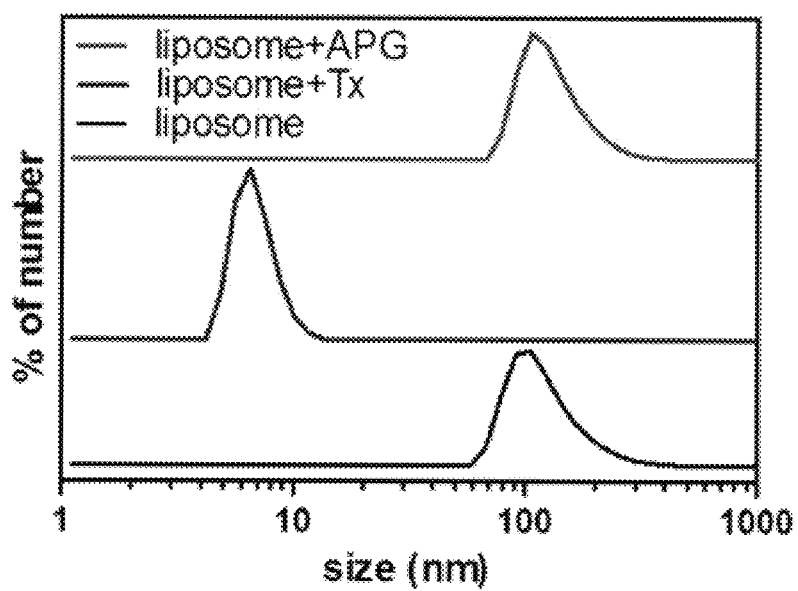
FIG. 8 is a view showing the intactness of liposomes after the treatment of the amphiphilic polymer. The sizes of liposomes were measured by dynamic light scattering (DLS) after treatment of APG (red line) or Triton X-100 (Tx, blue line). The size of intact liposomes was represented as black line.

The mechanism of APG-mediated insertion of membrane proteins is not fully understood: however, one of the possible mechanisms is a direct insertion of the APG:membrane protein into lipid bilayers due to the hydrophobic interactions between the nonpolar alkyl chains of APG and the lipids. APG could interact with liposomes, and this process might perturb the lipid bilayer structure without disrupting the integrity of liposomes (FIG. 8). Membrane proteins can be inserted into the lipid bilayer along with APG, and then dissociate from APG to form an active conformation in the lipid bilayer environment.

The lipid-bilayer structure may be one or more types selected from the group consisting of liposome, plasma membrane, and micelle.

Hereinafter, the present invention will be described in detail in conjunction with examples.

EXAMPLE

1. Synthesis of Amphiphilic Polymer (APG) from Poly-Gamma-Glutamic Acid 1-1. Synthesis of Amphiphilic Polymer After 0.3 g of a poly-gamma-glutamic acid (Bioleaders Corporation) having a weight-average molecular weight of 10,000 is dissolved in a dimethylsulfoxide solvent, a reaction mixture of 60 μmol of biotin (7.3 mg) and 0.1 mmol of DCC was added to the solvent, and thereby a biotin group was bound to an N-terminal of the poly-gamma-glutamic acid.

Then, 0.495 g of DCC (2.4 mmol), 0.167 g of an octylamine (1.3 mmol), and 0.233 g of a glucosamine (1.3 mmol) were added to the reaction solution with stirring at 45° C., and thereby an amphiphilic polymer in which the biotin group is introduced to the N-terminal, and a glucosamine group is introduced as a hydrophilic group, and an octyl group is introduced as a hydrophobic group was prepared.

In the amphiphilic polymer formed through the above-described synthesis method, about 41% of the total carboxyl groups were substituted with the octyl group, and 24% of the total carboxyl groups were substituted with a glucosyl group. A weight-average molecular weight of the above-described amphiphilic polymer is 17,000, and a theoretical amount of production is calculated as 0.51 g upon a 100% reaction. The amount of the amphiphilic polymer actually obtained is 0.28 g, which is calculated to be a yield of about 55%. This yield is significantly higher than a yield of less than 5% of a polymer such as an amphipol which is conventionally used to stabilize the membrane protein.

1-2. Synthesis of Amphiphilic Polymer

The amphiphilic polymer was synthesized in the same manner as in Example 1-1 except that fluorescein isothiocyanate (FITC) which is a fluorescent dye was used instead of the biotin, at the same number of moles.

1-3. Synthesis of Amphiphilic Polymer

The amphiphilic polymer was synthesized in the same manner as in Example 1-1 except that acetic acid was used instead of the biotin, at the same number of moles.

1-4. Synthesis of Amphiphilic Polymer

The amphiphilic polymer was synthesized in the same manner as in Example 1-1 except that cyclohexylamine was used instead of the octylamine, at the same number of moles.

1-5. Synthesis of Amphiphilic Polymer

The amphiphilic polymer was synthesized in the same manner as in Example 1-1 except that an octylamine and a glucosamine were used in a mole ratio of 7:3.

1-6. Synthesis of Amphiphilic Polymer

The amphiphilic polymer was synthesized in the same manner as in Example 1-1 except that an octylamine and a glucosamine were used in a mole ratio of 2:8.

2. Measurement of critical micelle concentration (CMC) of amphiphilic polymer

A critical micelle concentration (CMC) of the amphiphilic polymers in Examples 1-1 to 1-6, SDS and β-D-octylglucoside which are detergents was measured. The CMC was measured at various concentrations with a fluorescence ratio of 373 nm and 384 nm of pyrene.

Figure 3:
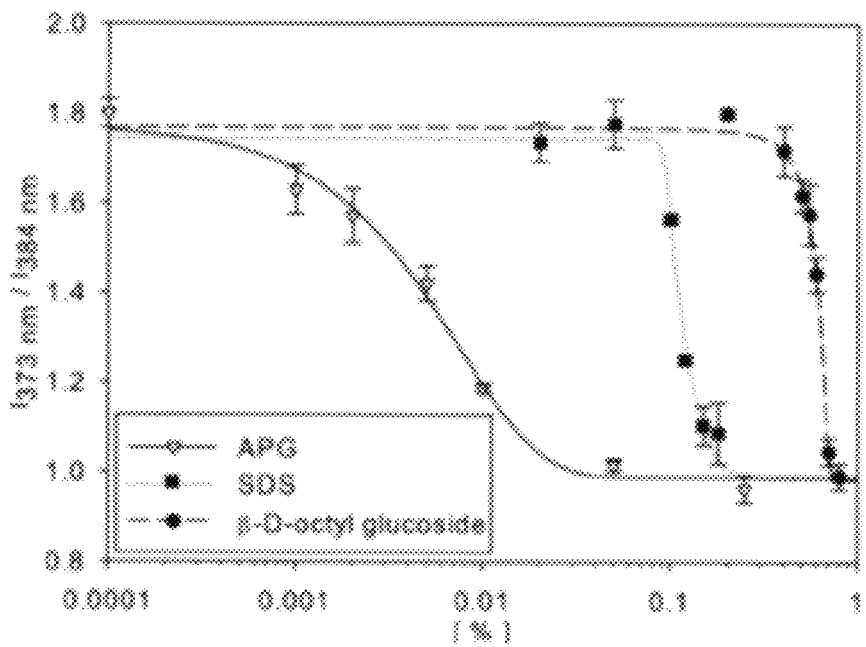
FIG. 3 is a CMC analysis result of the amphiphilic polymer in Example 1-1, SDS, and β-D-octylglucoside.

It was determined that the CMC of the amphiphilic polymer was significantly lower than that of the other detergents, and thus even a small amount of the amphiphilic polymer may be used. Referring to FIG. 3, the CMC of the amphiphilic polymer in Example 1-1 may be determined to be significantly lower (FIG. 3).

The amphiphilic polymer having the specific concentration or more forms a micelle, and the micelle is the unit that substantially binds to the membrane protein. The CMC of the amphiphilic polymer according to the embodiment of the present invention is 0.006%, which is significantly lower than those of the existing detergents, and thus the amphiphilic polymer may be bound to the membrane protein even using a low concentration of the amphiphilic polymer. This is because a plurality of hydrophobic structures is introduced into the amphiphilic polymer according to the embodiment of the present invention, the hydrophobic structures easily bind to each other, and thereby the micelles are formed.

3. Stabilization of Refined Membrane Protein

Human endothelin receptor type A (ETA) was expressed in colon bacillus, was dissolved in water using sarkosyl which is a detergent, and then was refined (Protein Expression and Purification 2012, vol 84, pp 14-18).

The refined ETA in the aqueous solution was bound to the detergent, and the amphiphilic polymers in Examples 1-1 to 1-6, at the same number of moles, were each added thereto to form an ETA-amphiphilic polymer complex. Then, a detergent was removed by a size exclusion chromatography method, and thereby the ETA-amphiphilic polymer complex was separated.

Figure 4:
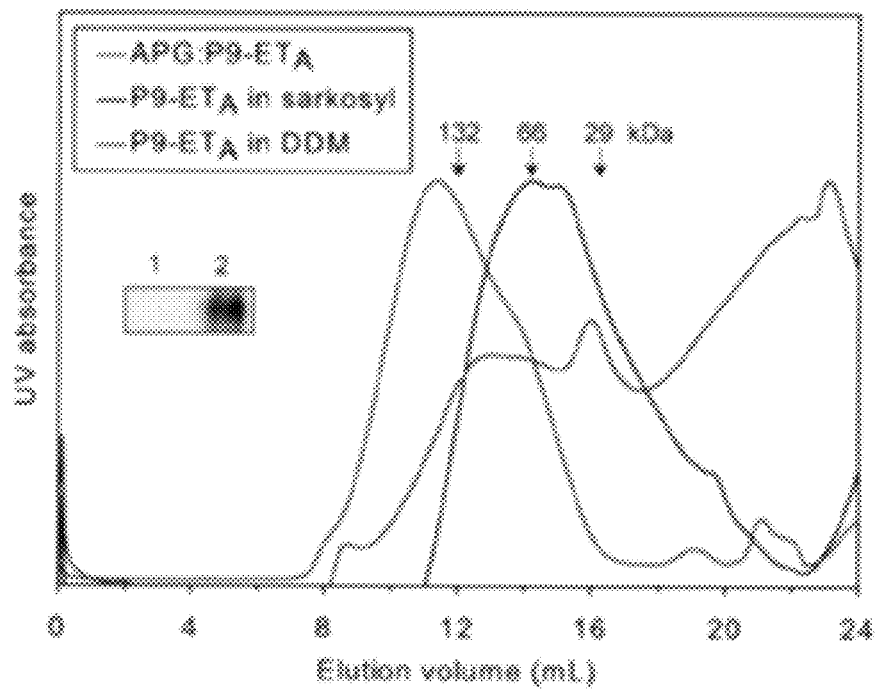
FIG. 4 is an analysis result of a size of ETA through size exclusion chromatography when ETA is refined using sarkosyl (black line), DDM (blue line), and the amphiphilic polymer in Example 1-1 (red line) which are detergents.

FIG. 4 is an analysis result of a size of ETA through size exclusion chromatography when ETA is refined using sarkosyl (black line), DDM (blue line), and the amphiphilic polymer in Example 1-1 (red line) which are detergents. Referring to FIG. 4, it may be determined that a complex of ETA and the amphiphilic polymer was formed, and ETA was easily refined.

4. Structural Restoration of Modified Membrane Protein

Bacteriorhodopsin (BR), which is a membrane protein expressed in halobacterium, is purple when BR has an active structure, and the purple color turns to a yellow color when BR is modified and loses the active structure. When SDS, which is a strong detergent, is added to BR having the active structure, BR is modified and loses the active structure, showing a yellow color.

1 mol of the amphiphilic polymers in Examples 1-1 to 1-6 was each added to 1 mol of BR which had lost its active structure, and then SDS was removed through size exclusion chromatography.

Figure 5:
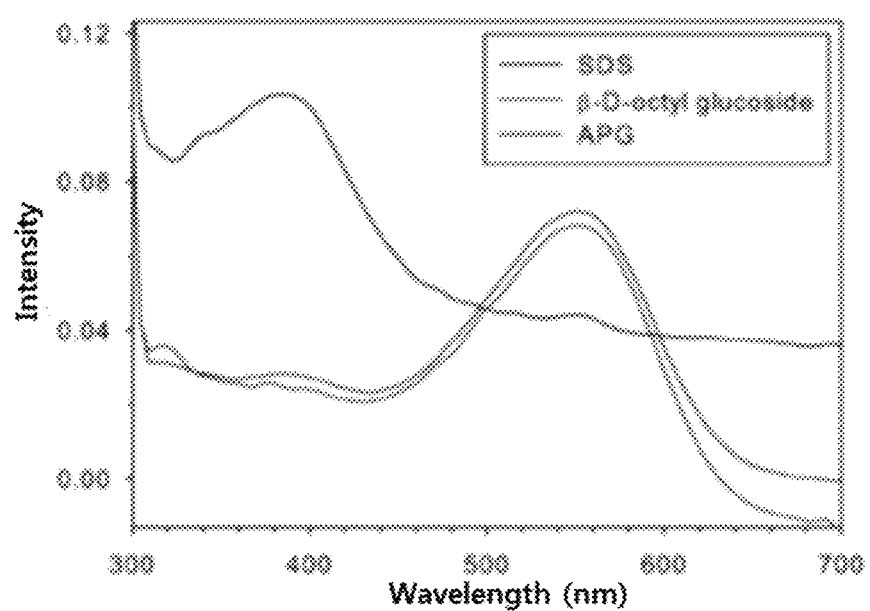
FIG. 5 is a view showing visible light absorption spectra in a case in which bacteriorhodopsin (BR) has an active structure stabilized by β-D-octyl glucoside which is a weak detergent (blue color), in a case in which BR is modified by SDS which is a strong detergent (black color), and in a case in which BR recovers an active structure by the amphiphilic polymer according to the embodiment of the present invention (red color)

Referring to FIG. 5, when the amphiphilic polymer in Example 1-1 was added to BR, and SDS was removed, it may be determined that BR turned purple, and the active structure thereof was restored.

5. Fixation of Membrane Protein 1 mol of the amphiphilic polymer to which biotin is attached in Example 1-1 was added to 1 mol of ETA in the aqueous solution, and thereby the ETA-amphiphilic polymer complex was formed.

Figure 6:
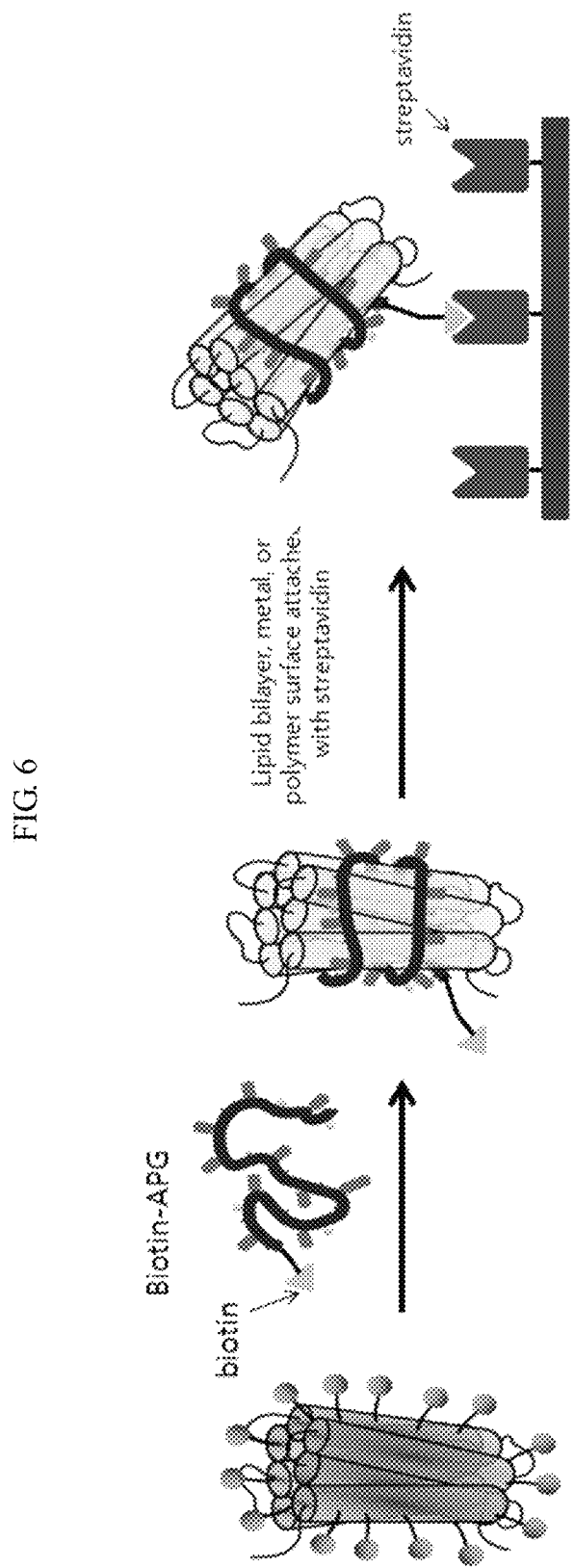
FIG. 6 is a view schematically illustrating a process of fixing a membrane protein to a substrate using the amphiphilic polymer.

Then, an ETA-amphiphilic polymer aqueous solution was applied on a base material of which a surface is attached to streptavidin, the bond of streptavidin and a biotin group of the amphiphilic polymer was formed, and thereby a membrane protein ETA was fixed on the base material (FIG. 6).

6. Reconstitution of Membrane Protein 1 mol of the amphiphilic polymer to which biotin is attached in Example 1-1 was added to 1 mol of ETA in the aqueous solution, and thereby the ETA-amphiphilic polymer complex was formed.

Figure 7:
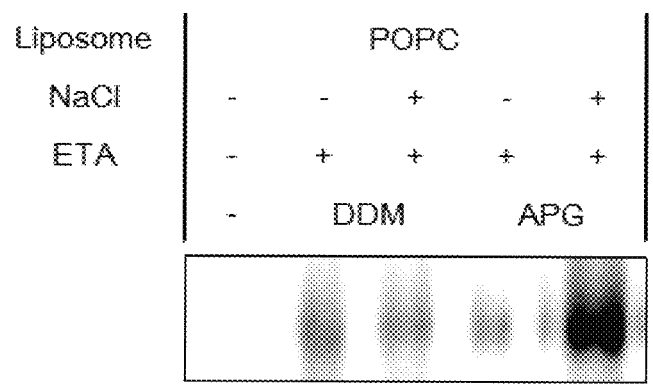
FIG. 7 is a view showing the efficiency of reconstitution of ETA stabilized with the amphiphilic polymer. ETA stabilized with dodecylmatoside (DDM) or the amphiphilic polymer (APG) was mixed with liposomes constituted with POPC(1-Palmitoyl-2-oleoyl-sn-glycero-3-phospho-choline) in the presence of 150 mM NaCl, and the amount of ETA reconstituted in the liposomes were detected by western blotting after recovery of liposomes by ultracentrifugation.
Figure 9:
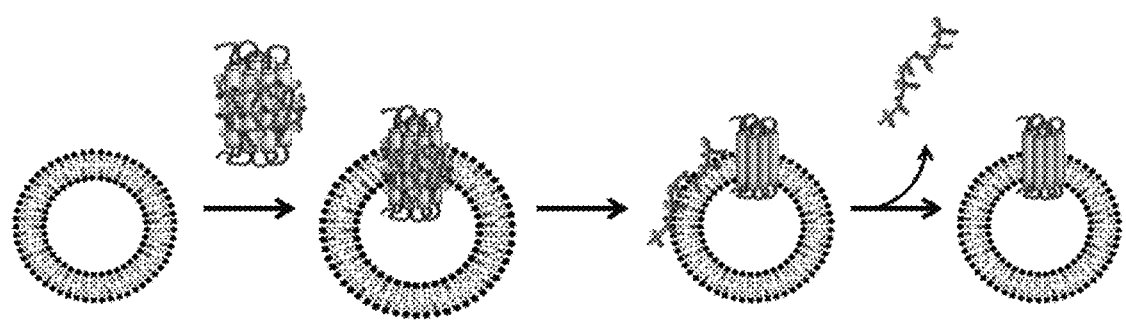
FIG. 9 is a view schematically illustrating a process of reconstitution of a membrane protein stabilized with the amphiphilic polymer into lipid-bilayer structure.

Then, an ETA-amphiphilic polymer aqueous solution was mixed with liposomes consisted of POPC (1-Palmitoyl-2-oleoyl-sn-glycero-3-phospho-choline), and the liposomes were recovered as precipitate fraction after centrifugation for 1 hr at 100,000×g. The amount of ETA reconstituted into liposomes was measured by western analysis (FIG. 7). The intactness of liposomes in the presence the amphiphilic polymer was examined by particle analyzer (FIG. 8), and the reconstitution process of membrane protein is depicted in FIG. 9.

The amphiphilic polymer according to the embodiment of the present invention includes a large amount of hydrophilic structures and hydrophobic structures, and thereby effectively stabilizing the membrane protein having a hydrophobic surface in the aqueous solution.

Further, when the amphiphilic polymer according to the embodiment of the present invention includes a fluorescent dye bound to an N-terminal amino group, the polymer may be used in fluorescent labeling of the membrane protein, and when the polymer includes a biotin group, the polymer may be effectively used to fix the membrane protein.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An amphiphilic polymer represented by the following Formula 1:

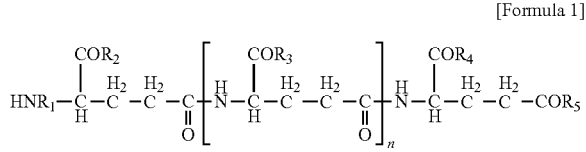

[Formula 1]

where $R_1$ is a fluorescent dye, a biotin group, an alkyl group having 1 to 10 carbon atoms, or a cycloalkyl carbonyl group having 5 to 20 carbon atoms;

$R_2$, $R_3$, $R_4$ and $R_5$ have a structure independently derived from a hydroxy group, or a hydrophilic or hydrophobic amine, repeated units of $R_3$ have identical or different structures, one or more of the repeated units of $R_3$ have a structure derived from a hydrophilic amine, one or more of the repeated units of $R_3$ have a structure derived from a hydrophobic amine; and n is an integer in a range of 1 to 1,000, wherein the hydrophilic amine is an alkyl amine having 1 to 10 carbon atoms or a cycloalkyl amine having 5 to 20 carbon atoms, which is substituted with a hydroxy group or an amino group; and the hydrophobic amine is an alkyl amine having 1 to 10 carbon atoms or a cycloalkyl amine having 5 to 20 carbon atoms.

2. The amphiphilic polymer of claim 1, wherein the fluorescent dye is one or more types selected from the group consisting of Cy3, Cy5, fluorescein isothiocyanate (FITC), tetramethylrhodamine isothiocyanate (RITC), Alexa, 4,4,-difluoro-4-bora-3a,4a-diaza-s-indacene (BODIPY), and Texas Red.

3. The amphiphilic polymer of claim 1, wherein at least one of $R_2$, $R_3$, $R_4$ and $R_5$ have a structure independently derived from the hydrophilic amine.

4. The amphiphilic polymer of claim 1, wherein at least one of $R_2$, $R_3$, $R_4$ and $R_5$ have a structure independently derived from the hydrophobic amine.

5. The amphiphilic polymer of claim 1, wherein a mole ratio of a structure derived from the hydrophilic amine to a structure derived from the hydrophobic amine is in a range of 1:9 to 9:1.

6. The amphiphilic polymer of claim 1, wherein a weight-average molecular weight is in a range of 5,000 to 50,000.

7. The amphiphilic polymer of claim 1, wherein $R_5$ is the hydrophilic amine.

8. The amphiphilic polymer of claim 1, wherein $R_5$ is the hydrophobic amine.

* * * * *